(12) United States Patent
Fodor

(10) Patent No.: US 6,700,022 B2
(45) Date of Patent: Mar. 2, 2004

(54) HIGH YIELD CYCLOHEXYL HYDROPEROXIDE DECOMPOSTITION PROCESS

(75) Inventor: Ludovic Fodor, Beaumont, TX (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 47 days.

(21) Appl. No.: 10/163,029

(22) Filed: Jun. 5, 2002

(65) Prior Publication Data

US 2003/0229253 A1 Dec. 11, 2003

(51) Int. Cl.⁷ .................. C07C 49/105; C07C 45/00
(52) U.S. Cl. ........................... 568/443; 568/376

(58) Field of Search ................... 568/376, 443

(56) References Cited

U.S. PATENT DOCUMENTS 3,957,867 A * 5/1976 Bukowick

FOREIGN PATENT DOCUMENTS

| EP | 0230254 B1 | * | 7/1990 |
| EP | 0659726 B1 | * | 11/1999 |
| EP | 0768292 B1 | * | 1/2000 |

* cited by examiner

Primary Examiner—Paul J. Killos

(57) ABSTRACT

Disclosed is a process for cyclohexyl hydroperoxide (CHHP) decomposition using in aqueous alkaline solution in presence of cobalt catalyst.

13 Claims, No Drawings

HIGH YIELD CYCLOHEXYL HYDROPEROXIDE DECOMPOSTITION PROCESS

FIELD OF THE INVENTION

The present invention relates to a process for preparing cyclohexahol and/or cyclohexanone by oxidizing cyclohexane with air, followed by decomposition of cyclohexyl hydroperoxide in aqueous alkaline solution in presence of cobalt catalyst.

BACKGROUND OF THE INVENTION

Adipic acid is reacted with hexamethylene diamine to form a Nylon salt, wherein the salt is polymerized to make Nylon 6,6. One method for making adipic acid involves cyclohexane oxidation using air. Cyclohexane oxidation carried out in this manner results in a mixture comprising cyclohexanone (K), cyclohexanol (A) (commonly referred to collectively as "KA"), and cyclohexyl hydroperoxide (CHHP). These processes are described in U.S. Pat. No. 3,957,876. Cyclohexyl hydroperoxide can be decomposed to give a mixture of cyclohexanone and cyclohexanol.

Various methods for the decomposition of cyclohexyl hydroperoxide have been described in the art. The decomposition of cyclohexyl hydroperoxide with heterogeneous cobalt catalyst is described by Kragten and Baur in E.P. No. 0659726B1.

The decomposition of cyclohexyl hydroperoxide with cobalt catalyst in presence of phosphonic acid derivatives is described by Hartig, Herrmann and Lucas in E.P. 0230254B1.

Kragten and Housmans discloses a process in EP0768292B1, for decomposing cyclohexyl hydroperoxide with chromium and/or cobalt at temperatures between 66 and 96° C.

The use of heterogeneous cobalt catalyst for CHHP decomposition requires special equipment and the catalyst is subjected to fouling due to the impurities present in the process. Using special phosphonic acid derivatives has been attempted to facilitate the CHHP decomposition, but it complicates the process and contributes to more by-product formation. Decomposing the CHHP in presence of chromium and cobalt catalysts at temperatures lower than 96° C. results in high hold-up time needed to perfect the decomposition reaction. The high hold-up time contributes to higher fixed costs for the production facility.

A cyclohexyl hydroperoxide decomposition process that results in an increase in KA yield is needed to improve the efficiency of adipic acid production processes. Described herein is a high yield cyclohexyl hydroperoxide decomposition process.

SUMMARY OF THE INVENTION

Described herein is a process for decomposing cyclohexyl-hydroperoxide to cyclohexanol and cyclohexanone, said process comprising:

(a) washing cyclohexane air oxidizer tails with water;

(b) separating the phases that result from step (a);

(c) contacting the water-washed air oxidizer tails with aqueous caustic solution;

(d) separating the phases that result from step (c);

(e) contacting the water washed air oxidizer tails organic phase with a catalyst comprising cobalt salt in caustic aqueous solution;

(f) agitating the two-phase product of step (e);

(g) separating the phases;

(h) removing the aqueous caustic phase containing the cobalt;

(i) washing the organic phase with water;

(j) optionally, recycling part of the aqueous caustic phase from step (h) back to step (c).

(k) optionally, recycling the water from previous washing step (i) back to step (a).

DESCRIPTION OF THE INVENTION

The cyclohexyl hydroperoxide ("CHHP") decomposition according to the present invention is achieved by cobalt catalyzed caustic method. This process is achieved by treating cyclohexane air oxidizer tails. By "cyclohexane air oxidizer tails" we mean all products formed during the cyclohexane oxidation process. These products generally comprise cyclohexane, cyclohexanol, cyclohexanone, cyclohexyl hydroperoxide, mono-basic acids, di-basic acids and other byproducts.

The CHHP decomposition process involves several steps. First, the cyclohexane air oxidizer tails are washed with water. Two phases result: an organic phase and an aqueous phase. The two phases are separated by any method known in the art to achieve separation, such as decanting, maybe used. The separation may be used as a continuous operation.

The water-washed air oxidizer tails are contacted with aqueous caustic solution, to reduce acid impurities. Two phases result and are separated. The phase comprising most of the water-washed air oxidizer tails is contacted with a catalyst comprising cobalt salt in caustic aqueous solution. The two-phase product of the previous step is agitated, and the resulting phases are separated to remove the aqueous caustic phase. The aqueous caustic phase from this step may be recycled to be used in the process again. The organic phase is washed with water. The water may then be recycled to repeat the process.

The caustic that is used in the process is a solution form of an alkali metal, alkaline hydroxide, or alkaline carbonate. The concentration of the caustic solution is from about 2 wt % to about 25 wt %, preferably from about 7 wt % to about 20wt %. Preferably the caustic solution comprises sodium hydroxide. As indicated, some of the caustic solution may be recycled during the process.

The most efficient CHHP decomposition is achieved with a ratio of aqueous phase to organic phase that is higher than 0.10:100, preferably between 0.15:100 to 1.00:100.

The catalyst of the present invention is water-soluble cobalt salt. Examples of such catalysts are cobalt sulfate and cobalt chloride. The amount of catalyst used in the present process is from about 0.1 to about 100 ppm, preferably 3 to 20 ppm, and most preferably 5 to 15 ppm. It is important to adjust the catalyst concentration optimally as a function of the process temperature. Generally, higher temperatures require lower catalyst concentrations.

Other factors that influence the efficiency of the process described herein are process temperature, amount and/or concentration of caustic used and adequate agitation. As a general rule, higher temperatures favor high CHHP decomposition rate. It should be noted that higher temperatures may increase the by-products formation. One may optimize the CHHP decomposition of this process by carefully choosing the temperature, catalyst concentration and residence time.

The process can be carried out at temperatures from about 100° C. to about 150° C. degrees, preferably from about 105° C. to about 145° C. The process can be carried out in horizontal reactors, with or without interior compartments, tank reactors, stirred tank reactors, static mixers, stirred autoclaves, and similar process vessels.

Adequate agitation will favorably affect the efficiency of the process. This can be achieved by using efficient mixing systems, or static mixers.

The basic reaction during the CHHP decomposition can be explained as follows. One (1) mol of KA mixture is obtained from 1 mole of CHHP after decomposition by the process. The mixture comprises x mol of A, y mole of K and z mol of by-products, and x+y+z=1. CHHP decomposition process yield is expressed as:

$$100 \; [K+A+CHHP]_{product}/[K+A+CHHP]_{feed}$$

wherein $[K+A+CHHP]_{product}$ is the concentration of K+A+CHHP in the organic phase exiting the last decanter in the process; and wherein $[K+A+CHHP]_{feed}$ is concentration of K+A+CHHP in the organic phase feeding the water wash. All concentrations are in moles.

The typical yield loss during the CHHP decomposition process includes the physical (K+A+CHHP) loss by dissolution in aqueous solution and the losses due to any by-product formation during the catalytic and thermal CHHP decomposition process. The yield from the CHHP decomposition process can vary depending on the amount of water used in impurity elimination step, the amount of cobalt catalyst used, the ratio of the aqueous solution to organic phase, among other process conditions. The experiments in the examples were done by varying two parameters: water flow-rate and the amount of cobalt catalyst. Excess water flow could cause some of the K, the A and CHHP to be lost in the aqueous phase by dissolution. If there is not enough water, some of the impurities will not be eliminated.

EXAMPLES

Legend for the Examples

"t/h" means tonnes per hour

"K" means cyclohexanol

"A" means cyclohexanone

"CHHP" means cyclohexyl hydroperoxide

All of the examples below were carried out using cobalt catalyst. During all the experiments the process was running at steady state. The cyclohexanone ("K"), cyclohexanol ("A") and cyclohexyl hydroperoxide (CHHP) analyses given are average of three different samples. During the experiments all process parameters, except the parameters chosen for optimization, were held constant. After the parameter changes were made, the experiments were run for 12 h to reach steady state.

EXAMPLE 1

For Example 1, 360 t/h of air oxidizer tails with 0.71% cyclohexanol, 1.12% cyclohexanone and 3.24% cyclohexyl-hydroperoxide was mixed in a static mixer with 1.0 t/h recycled water in the process at 120 deg C. temperature. The aqueous to organic phase ratio is 0.28:100. The separated water was decanted using decanters. The organic phase was treated at 118 deg C. with a caustic cobalt solution having 5 ppm Co and the CHHP was decomposed in the CHHP decomposition reactors. The caustic solution was separated using decanters and the organic phase was washed with water. The concentration of cyclohexanol in the organic phase after wash was 1.71% wt. and cyclohexanone 2.47% wt. corresponding to 91.30% CHHP decomposition process yield.

EXAMPLE 2

In this experiment the amount of recycled water was increased to 1.5 t/h, the ratio of the aqueous to organic phase is 0.43:100 while the other parameters were kept same as in Example 1. The CHHP decomposition process yield in this case was 90.56.

EXAMPLE 3

Example 3 was carried out in a similar manner as Example 1 except that the concentration of the cobalt catalyst was increased to 10 ppm. The CHHP decomposition process yield was measured at 96.9%. Example 3 demonstrates that an increase in catalyst concentration with lower recycled water flow rate (1.0 t/h) increases yield.

EXAMPLE 4

The steps were carried out in a similar manner as in Example 3, except that the recycled water flow rate was increased to 1.5 t/h The CHHP decomposition process yield was 95.75%. Example 4 demonstrates that an increase in recycled water flow to 1.5 t/h at high cobalt concentration (10 ppm) has a small detrimental effect on the CHHP decomposition process yield. A higher CHHP decomposition process yield was obtained at 10 ppm Co catalyst and 1.0 t/h recycled water (Example 3).

What is claimed is:

1. A process for decomposing cyclohexyl-hydroperoxide to cyclohexanol and cyclohexanone, said process comprising:
    (a) washing cyclohexane air oxidizer tails with water;
    (b) separating the phases that result from step (a);
    (c) contacting the water-washed air oxidizer tails with aqueous caustic solution;
    (d) separating the phases that result from step (c);
    (e) contacting the water washed air oxidizer tails organic phase with a catalyst comprising cobalt salt in caustic aqueous solution;
    (f) agitating the two-phase product of step (e);
    (g) separating the phases;
    (h) removing the aqueous caustic phase containing the cobalt;
    (i) washing the organic phase with water;
    (j) optionally, recycling part of the aqueous caustic phase from step (h) back to step (c);
    (k) optionally, recycling the water from previous washing step (j) back to step (a).

2. A process of claim 1 wherein the caustic solution is selected from the group consisting of alkali metal, alkaline hydroxides, alkaline carbonates.

3. A process of claim 2 wherein the caustic solution comprises of sodium hydroxide.

4. A process of claim 1 wherein the concentration of caustic solution is in the range of 2 wt % to 25 wt %.

5. A process of claim 4 wherein the concentration of caustic solution is in the range of 7% to about 20%.

6. A process according to claim 1 wherein step (c) is carried out at a temperature between 105° C. to 145° C.

7. A process according to claim 1 where amount of cobalt catalyst used is between 3 to 20 ppm.

8. A process according to claim 7 where amount of cobalt catalyst used is between 5 to 15 ppm.

9. A process according to claim 1 where the water from caustic removal step is recycled to wash the air oxidizer tails in step (a).

10. A process according to claim 1 wherein the separation of aqueous phase from organic phase is done by decanting.

11. A process according to claim 10 wherein the decanting is performed in a continuous operation.

12. A process according to claim 1 wherein aqueous:organic phase ratio in step (a) is from about 0.10:100 to about 1.00:100.

13. A process according to claim 12 wherein a volume ratio of aqueous to organic phase is between 0.10:100 to 0.80:100.

* * * * *

UNITED STATES PATENT AND TRADEMARK OFFICE
CERTIFICATE OF CORRECTION

PATENT NO. : 6,700,022 B2  Page 1 of 1
APPLICATION NO. : 10/163029
DATED : March 2, 2004
INVENTOR(S) : Fodor Ludovic It is certified that error appears in the above-identified patent and that said Letters Patent is hereby corrected as shown below:

Column 4:

2.  A process of claim 1 wherein the caustic solution is selected from the group consisting of [alkali metal,] alkaline hydroxides, alkaline carbonates.

Signed and Sealed this

Twenty-fifth Day of December, 2007

JON W. DUDAS
*Director of the United States Patent and Trademark Office*